United States Patent
Ha et al.

(10) Patent No.: US 10,071,279 B2
(45) Date of Patent: Sep. 11, 2018

(54) MUSCULAR STRENGTH ASSISTING APPARATUSES AND METHODS OF CONTROLLING THE SAME

(71) Applicant: Samsung Electronics Co., Ltd., Suwon-Si, Gyeonggi-Do (KR)

(72) Inventors: Tae Sin Ha, Seongnam-si (KR); Young Do Kwon, Yongin-si (KR); Youn Baek Lee, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 310 days.

(21) Appl. No.: 14/499,370

(22) Filed: Sep. 29, 2014

(65) Prior Publication Data

US 2015/0141886 A1    May 21, 2015

(30) Foreign Application Priority Data

Nov. 19, 2013 (KR) .................. 10-2013-0140624

(51) Int. Cl.
*A61H 11/00* (2006.01)
*A63B 23/035* (2006.01)
(Continued)

(52) U.S. Cl.
CPC .......... *A63B 23/035* (2013.01); *A61B 5/1108* (2013.01); *A61F 5/02* (2013.01);
(Continued)

(58) Field of Classification Search
CPC ...... A61H 2201/5007; A61H 2011/005; A61H 2201/1215; A61H 2201/165; A61H 2230/60; A61H 2230/605
(Continued)

(56) References Cited

U.S. PATENT DOCUMENTS 5,827,209 A * 10/1998 Gross ................... A61B 5/1121
                                                            602/19
9,345,609 B2 * 5/2016 Hyde ........................ A61F 5/02
(Continued)

OTHER PUBLICATIONS

Hogan, N. "A review of the methods of processing EMG for use as a proportional control signal." Biomedical Engineering (1976) 11(3):81-86.*

*Primary Examiner* — Valerie L Woodward
*Assistant Examiner* — Douglas Sul
(74) *Attorney, Agent, or Firm* — Harness, Dickey & Pierce, PLC

(57) ABSTRACT

A muscular strength assisting apparatus may include: a wearing unit configured to enclose a part of a user's body; a tightening unit configured to pull the wearing unit in one or both directions; and/or a control unit configured to drive the tightening unit to tighten the part of the user's body on which the wearing unit is located, when it is determined that muscular contraction occurs at the part of the user's body on which the wearing unit is located. A method of controlling a muscular strength assisting apparatus may include: determining whether muscular contraction occurs at a part of a user's body that is enclosed by a wearing unit; and/or driving a tightening unit pulling the wearing unit in one direction or both directions to tighten the part of the user's body on which the wearing unit is located when it is determined that the muscular contraction occurs.

14 Claims, 10 Drawing Sheets

(51) Int. Cl.
*A61F 5/02* (2006.01)
*A63B 21/00* (2006.01)
*A63B 24/00* (2006.01)
*A61B 5/11* (2006.01)
*A63B 21/005* (2006.01)
*A61B 5/22* (2006.01)

(52) U.S. Cl.
CPC ...... *A63B 21/0004* (2013.01); *A63B 21/4011* (2015.10); *A63B 21/4017* (2015.10); *A63B 21/4025* (2015.10); *A63B 24/0087* (2013.01); A61B 5/1118 (2013.01); A61B 5/224 (2013.01); A61H 2011/005 (2013.01); A61H 2201/1215 (2013.01); A61H 2201/1246 (2013.01); A61H 2201/164 (2013.01); A61H 2201/165 (2013.01); A61H 2201/1635 (2013.01); A61H 2201/5007 (2013.01); A61H 2201/5035 (2013.01); A61H 2201/5046 (2013.01); A61H 2201/5058 (2013.01); A61H 2201/5061 (2013.01); A61H 2201/5084 (2013.01); A61H 2230/605 (2013.01); A63B 21/0058 (2013.01); A63B 21/00181 (2013.01); A63B 2024/0093 (2013.01); A63B 2213/006 (2013.01); A63B 2220/40 (2013.01); *A63B 2220/51* (2013.01); *A63B 2220/54* (2013.01); *A63B 2220/803* (2013.01); *A63B 2220/89* (2013.01); *A63B 2225/20* (2013.01); *A63B 2230/045* (2013.01); *A63B 2230/605* (2013.01)

(58) Field of Classification Search
USPC ........................................................ 602/75
See application file for complete search history.

(56) References Cited

U.S. PATENT DOCUMENTS

| | | |
|---|---|---|
| 2005/0159690 A1 | 7/2005 | Barak et al. |
| 2006/0128538 A1 | 6/2006 | Sato et al. |
| 2007/0066462 A1 | 3/2007 | Cohen |
| 2007/0191743 A1* | 8/2007 | McBean ............ A61B 5/04888 601/5 |
| 2007/0265140 A1* | 11/2007 | Kim ........................ A61H 1/02 482/8 |
| 2008/0146980 A1 | 6/2008 | Rousso et al. |
| 2010/0198116 A1 | 8/2010 | Hirata et al. |
| 2014/0180186 A1* | 6/2014 | Hyde ........................ A61F 5/02 602/19 |
| 2014/0330186 A1* | 11/2014 | Hyde ........................ A61F 5/02 602/19 |

* cited by examiner

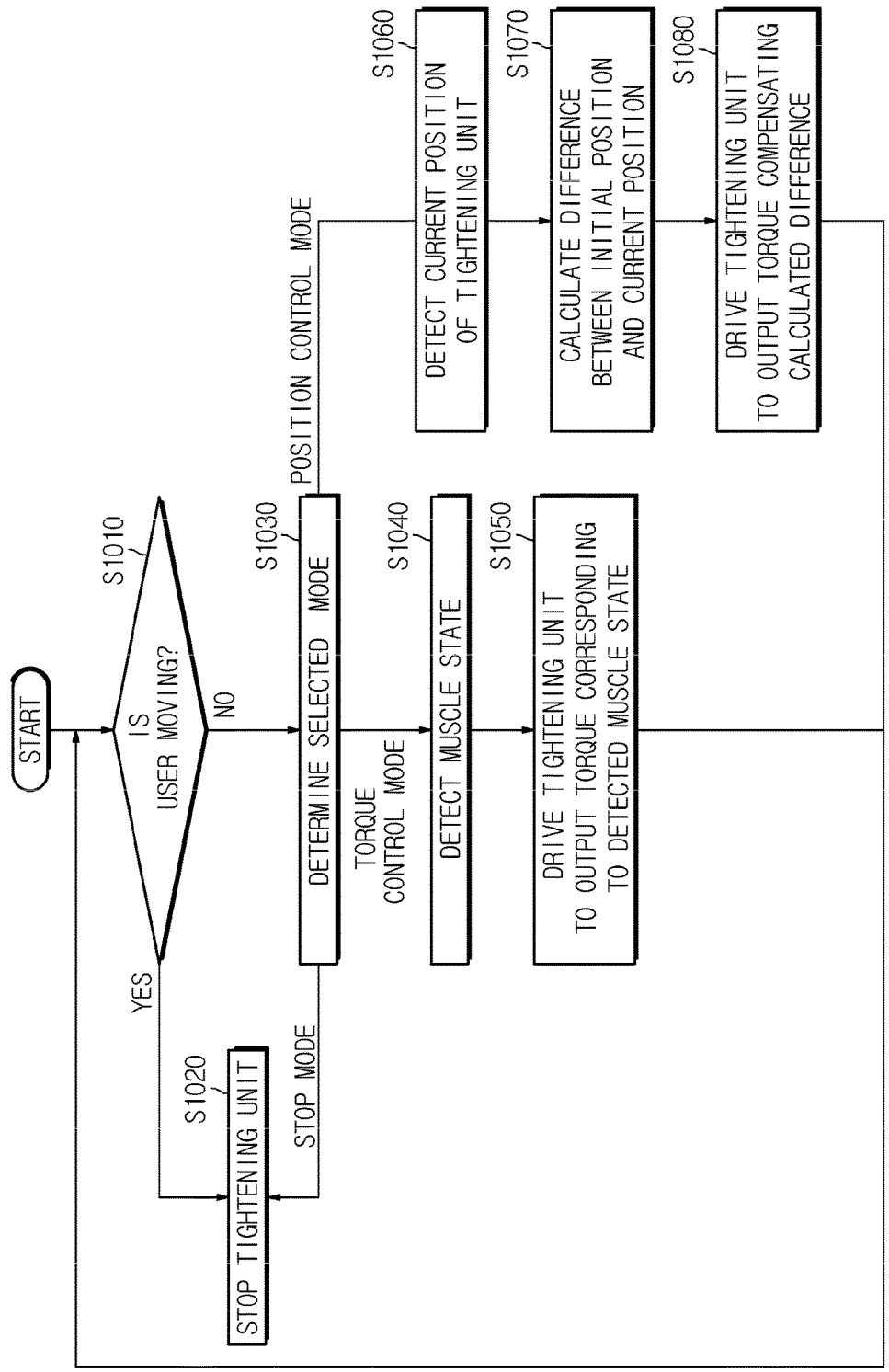

MUSCULAR STRENGTH ASSISTING APPARATUSES AND METHODS OF CONTROLLING THE SAME

CROSS-REFERENCE TO RELATED APPLICATION(S)

This application claims priority from Korean Patent Application No. 10-2013-0140624, filed on Nov. 19, 2013, in the Korean Intellectual Property Office (KIPO), the entire contents of which are incorporated herein by reference.

BACKGROUND

1. Field

Some example embodiments may relate generally to muscular strength assisting apparatuses and/or methods of controlling the same. Some example embodiments may relate to muscular strength assisting apparatuses that assist forces applied to muscles upon muscular contraction and/or methods of controlling the same.

2. Description of Related Art

In general, it is not easy for the disabled or the elderly who are physically weak to perform even simple actions (such as walking) that a healthy person may easily do. Therefore, recently, technology development for various apparatuses for assisting a muscular strength intended for the disabled or the elderly may have been promoted.

A conventional muscular strength assisting apparatus may be almost a wearable robot-type in which an actuator is installed at a user's upper limb joint or lower limb joint in order to assist muscular force.

SUMMARY

Some example embodiments may provide muscular strength assisting apparatuses that may be easily installed at a desired part of a user's body without any limitation. Some example embodiments may provide methods of controlling the same.

Some example embodiments may provide muscular strength assisting apparatuses that may disperse force applied to muscles, may reduce muscle fatigue, and/or thereby may enhance muscular endurance. Some example embodiments may provide methods of controlling the same.

In some example embodiments, a muscular strength assisting apparatus may comprise: a wearing unit configured to enclose a part of a user's body; a tightening unit configured to pull the wearing unit in one direction or both directions; and/or a control unit configured to drive the tightening unit to tighten the part of the user's body on which the wearing unit is located, when it is determined that muscular contraction occurs at the part of the user's body on which the wearing unit is located.

In some example embodiments, the apparatus may further comprise: a muscle state detecting unit configured to detect the muscular contraction.

In some example embodiments, the control unit may be configured to detect a current muscle activation state of the part of the user's body on which the wearing unit is located using the muscle state detecting unit, may be configured to calculate a difference between the detected current muscle activation state and an initial muscle activation state, and may be configured to drive the tightening unit to output a force or torque proportional to the calculated difference.

In some example embodiments, the apparatus may further comprise: a movement detecting unit configured to detect whether the user is moving.

In some example embodiments, the control unit may be configured to detect a moving speed of the user using the movement detecting unit, may be configured to determine whether the user is moving based on the detected moving speed, may be configured to stop the tightening unit when the user is moving, and may be configured to drive the tightening unit when the user is not moving.

In some example embodiments, the tightening unit may include a motor.

In some example embodiments, the apparatus may further comprise: a position detecting unit configured to detect position information of the tightening unit.

In some example embodiments, the control unit may be configured to detect a current position of the tightening unit using the position detecting unit, may be configured to calculate a difference between the detected current position and an initial position, and may be configured to drive the tightening unit to output a force or torque compensating the calculated difference.

In some example embodiments, the apparatus may further comprise: an operation unit having a plurality of inputs configured to receive commands from the user.

In some example embodiments, the operation unit may further comprise a display configured to display an operating state of the muscular strength assisting apparatus and an operated state of the inputs by the user.

In some example embodiments, a method of controlling a muscular strength assisting apparatus may comprise: determining whether muscular contraction occurs at a part of a user's body that is enclosed by a wearing unit; and/or driving a tightening unit pulling the wearing unit in one direction or both directions to tighten the part of the user's body on which the wearing unit is located when it is determined that the muscular contraction occurs.

In some example embodiments, the method may further comprise: determining a mode set by the user before the determining of whether the muscular contraction occurs.

In some example embodiments, the mode may comprise a stop mode, a torque control mode, or a position control mode.

In some example embodiments, after the determining of the mode set by the user, if the set mode is the stop mode, the tightening unit may be in a stopped state, even though the muscular contraction occurs at the part of the user's body on which the wearing unit is located.

In some example embodiments, after the determining of the mode set by the user, if the set mode is the torque control mode, the determining of whether the muscular contraction occurs may be performed by detecting a muscle activation state of the part of the user's body on which the wearing unit is located.

In some example embodiments, the driving of the tightening unit to tighten the part of the user's body on which the wearing unit is located may comprise: calculating a difference value between the detected muscle activation state and an initial muscle activation state; and/or driving the tightening unit to output a force or torque proportional to the calculated difference value.

In some example embodiments, after the determining of the mode set by the user, if the set mode is the position control mode, the determining of whether the muscular contraction occurs may be performed by detecting a position of the tightening unit.

In some example embodiments, the driving of the tightening unit to tighten the part of the user's body on which the wearing unit is located may comprise: calculating a difference value between the detected position of the tightening unit and an initial position of the tightening unit; and/or driving the tightening unit to output a force or torque compensating the calculated difference value.

In some example embodiments, the method may further comprise: determining whether the user is moving, before the determining of whether the muscular contraction occurs.

In some example embodiments, after the determining of whether the user is moving, if the user is moving, the tightening unit may be in a stopped state, even though the muscular contraction occurs at the part of the user's body on which the wearing unit is located, and if the user is not moving, the tightening unit may be driven so that the wearing unit tightens the corresponding part of the user's body, when the muscular contraction occurs at the part of the user's body on which the wearing unit is located.

BRIEF DESCRIPTION OF THE DRAWINGS

The above and/or other aspects and advantages will become more apparent and more readily appreciated from the following detailed description of example embodiments, taken in conjunction with the accompanying drawings, in which:

FIG. 10 is a flowchart illustrating a controlling method of the muscular strength assisting apparatus according to some example embodiments.

DETAILED DESCRIPTION

Figure 1:
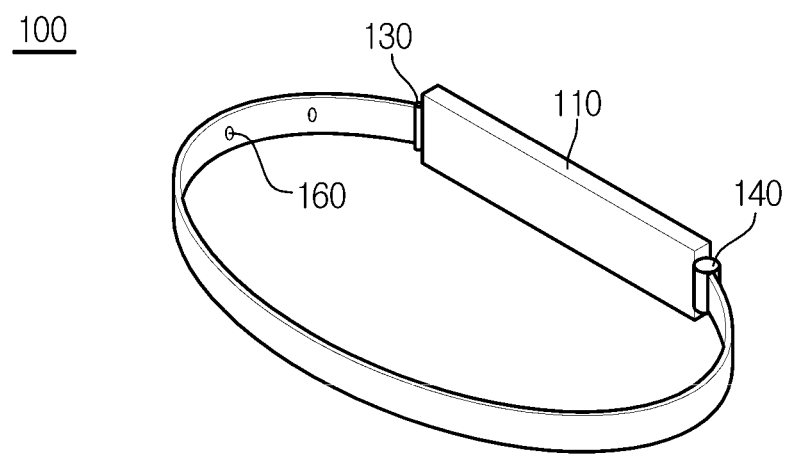
FIG. 1 is a view illustrating an external appearance of a muscular strength assisting apparatus according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component((s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
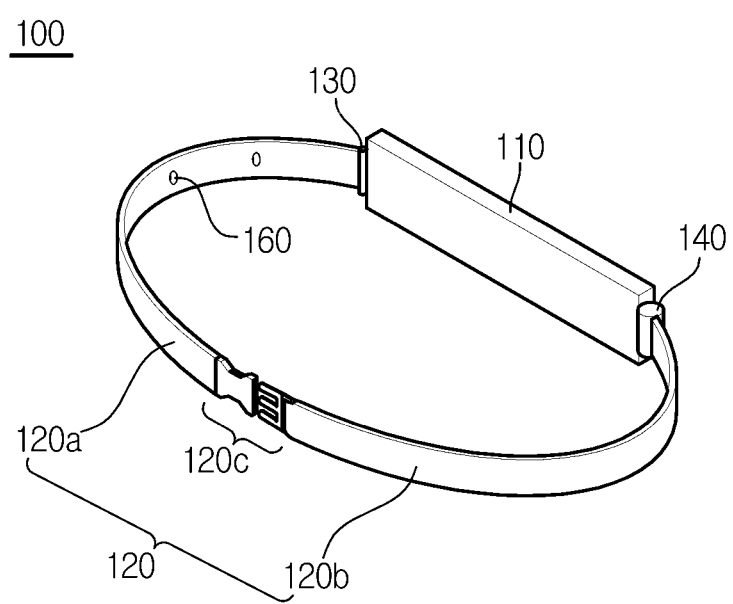
FIG. 2 is a view illustrating an external appearance of a muscular strength assisting apparatus according to some example embodiments.
Figure 3:
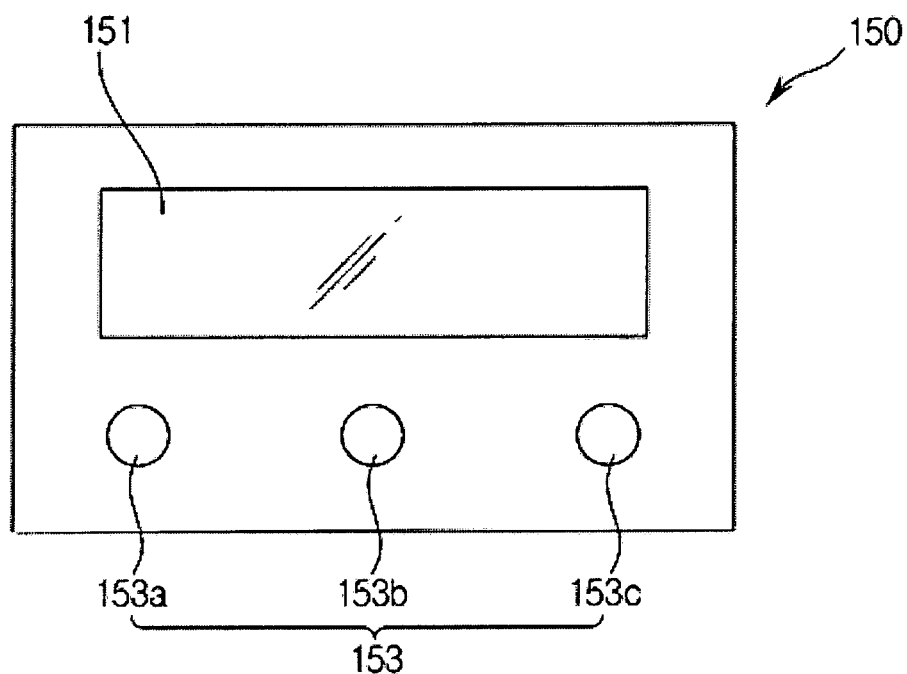
FIG. 3 is a view illustrating an example of an operation unit of a muscular strength assisting apparatus according to some example embodiments.

FIG. 1 is a view illustrating an external appearance of a muscular strength assisting apparatus according to some example embodiments, FIG. 2 is a view illustrating an external appearance of a muscular strength assisting apparatus according to some example embodiments, and FIG. 3 is a view illustrating an example of an operation unit of a muscular strength assisting apparatus according to some example embodiments.

Referring to FIGS. 1 and 2, a muscular strength assisting apparatus 100 according to some example embodiments may include a body unit 110, a wearing unit 120, a fastening unit 130, and a tightening unit 140.

The body unit 110 is connected with the wearing unit 120 to be described later. As illustrated in FIGS. 1 and 2, first and second sides of the body unit 110 may be connected with first and second sides of the wearing unit 120, respectively, but is not particularly limited thereto.

Further, as illustrated in FIGS. 1 and 2, the fastening unit 130 may be provided at the one side of the body unit 110 in order to fasten one end of the wearing unit 120, and the tightening unit 140 may be provided at the other side thereof in order to pull the other side of the wearing unit 120. However, example embodiments are not particularly limited thereto, and the tightening unit 140 may be provided at both sides of the body unit 110 so that the wearing unit 120 may be pulled in both directions.

The body unit 110 may have an operation unit 150 which displays an operating state of the muscular strength assisting apparatus 100 or an operated state thereof by a user and also receives a command from the user, and a control unit 170 which controls whole operations of the muscular strength assisting apparatus 100, but is not particularly limited thereto.

The wearing unit 120 is formed to enclose a part of the user's body. In some example embodiments, a belt or the like may be used for the wearing unit 120, but example embodiments are not particularly limited thereto.

As illustrated in FIG. 1, the wearing unit 120 may have a structure which is continuously connected from one side of the body unit 110 to the other side thereof, but is not particularly limited thereto. As illustrated in FIG. 2, the wearing unit 120 may have a structure including a first wearing unit 120a connected to one side of the body unit 110, a second wearing unit 120b connected to the other side of the body unit 110, and a fastening member 120c connecting the first and second wearing units 120a and 120b. The fastening member 120c is not limited to the structure as illustrated in FIG. 2, and may have various well-known structures.

When the wearing unit 120 has the structure illustrated in FIG. 1, the muscular strength assisting apparatus 100 may be installed in a manner fitted to a part of a user's body, and when the wearing unit 120 has the structure illustrated in FIG. 2, the muscular strength assisting apparatus 100 may be installed in a manner fastened on the part of the user's body.

Further, the wearing unit 120 may be made of a non-elastic material or an elastic material, and the material is not particularly limited.

Further, one end of the wearing unit 120 may be connected with the fastening unit 130, which is provided at one side of the body unit 110, so as to have a degree of freedom in a rotational direction but to be fastened in a pulling direction, and the other end thereof may be connected with the tightening unit 140, which is provided at the other side of the body unit 110, so as to be capable of being pulled. That is, the wearing unit 120 may be connected to the body unit 110 so as to be pulled only in one direction of the body unit 110, but is not particularly limited thereto. The wearing unit 120 may be connected to the body unit 110 so as to be pulled in both directions of the body unit 110.

In other words, the one end of the wearing unit 120 is connected to the fastening unit 130, which is provided at the one side of the body unit 110, so as to be fastened, and the other end thereof may be connected with the tightening unit 140, which is provided at the other side of the body unit 110, so as to be wound on the tightening unit 140 according to rotation of the tightening unit 140 and thus pulled. Therefore, the wearing unit 120 may tighten a muscle of a part of a user's body on which the wearing unit 120 is installed.

As illustrated in FIGS. 1 and 2, the fastening unit 130 may be provided at one side of the body unit 110 and may be configured such that the one end of the wearing unit 120 is connected to the body unit 110 to be not pulled but fastened. Although not specifically illustrated in FIGS. 1 and 2, for example, the fastening unit 130 may have a hinge structure, but is not limited thereto. Therefore, the one end of the wearing unit 120 may be maintained in a state of being rotatable with respect to the fastening unit 130, but fastened in a horizontal or vertical direction.

As illustrated in FIGS. 1 and 2, the tightening unit 140 may be provided at the other side of the body unit 110, may be configured such that the other end of the wearing unit 120 is connected to the body unit 110 and also capable of being pulled, and thus may tighten the muscle of the part of the user's body on which the wearing unit 120 is located.

In some example embodiments, a motor may be used for the tightening unit 140, but example embodiments are not particularly limited thereto. When the motor is used for the tightening unit 140, the other end of the wearing unit 120 is wound on the tightening unit 140 according to the rotation of the tightening unit 140 and, thus, pulled. As a result thereof, the wearing unit 120 may tighten the part of the user's body on which the wearing unit 120 is located.

Further, the muscular strength assisting apparatus 100 according to some example embodiments may further include the operation unit 150. The operation unit 150 is configured to display the operating state of the muscular strength assisting apparatus 100, and also receive a command from the user. For example, as illustrated in FIG. 3, the operation unit 150 may include a display 151 displaying the operating state of the muscular strength assisting apparatus 100 or the operated state thereof by the user, and a plurality of inputs 153 receiving a command from the user.

In some example embodiments, the display 151 may include a liquid crystal display (LCD), a light emitting diode (LED), an organic light emitting diode (OLED), a plasma display panel (PDP), or a combination thereof, but is not particularly limited thereto.

Meanwhile, the display 151 according to some example embodiments may have a touchscreen structure which may receive the command from the user, but is not particularly limited thereto.

The inputs 153 serve to receive the command from the user, and may be provided in the form of buttons or the like, but are not particularly limited thereto. Also, FIG. 3 illustrates that three inputs 153 are provided, but this is just an example, and the number of inputs 153 is not particularly limited.

In some example embodiments, the three inputs 153 may include a power on/off button 153a, a setting button 153b, and a mode selecting button 153c, but are not particularly limited thereto. Each input 153 will be described later in a configuration of the muscular strength assisting apparatus 100.

Until now, the external appearance of the muscular strength assisting apparatus according to some example embodiments has been described. As described above, since the muscular strength assisting apparatus according to some example embodiments serves to assist the muscular strength by tightening a muscle and thus dispersing force applied to the muscle, not by applying force to a joint like in a conventional wearing-type muscular strength assisting apparatus, it is difficult to assist a great strength compared to the conventional wearing-type muscular strength assisting apparatus, but it is possible to be installed at any part of a user's body without limitation.

That is, in the conventional wearing-type muscular strength assisting apparatus in which force is applied to a joint to assist the muscular strength, in order for the force applied to the joint to be transmitted to the part of the user's body, a link connected with the joint should be fastened to the part of the user's body, and the link should have a stiffness. Therefore, the conventional wearing-type muscular strength assisting apparatus may provide great strength, but has an inconvenience in wearing and a poor wearing comfort due to the link having the stiffness. Further, since the conventional wearing-type muscular strength assisting apparatus is heavy, the user may be hindered in actions.

On the other hand, as illustrated in FIGS. 1 and 2, since the muscular strength assisting apparatus according to some example embodiments includes only the wearing unit without a separate element fastened to a part of a user's body, it is easy to wear it on a desirable part of the user's body, and since the muscular strength assisting apparatus according to some example embodiments is light, the user may not be hindered in actions while wearing it. Further, since the wearing unit does not have sufficient stiffness, it is possible to provide a good wearing comfort.

Hereinafter, some example embodiments of the muscular strength assisting apparatus will be described.

Figure 4:
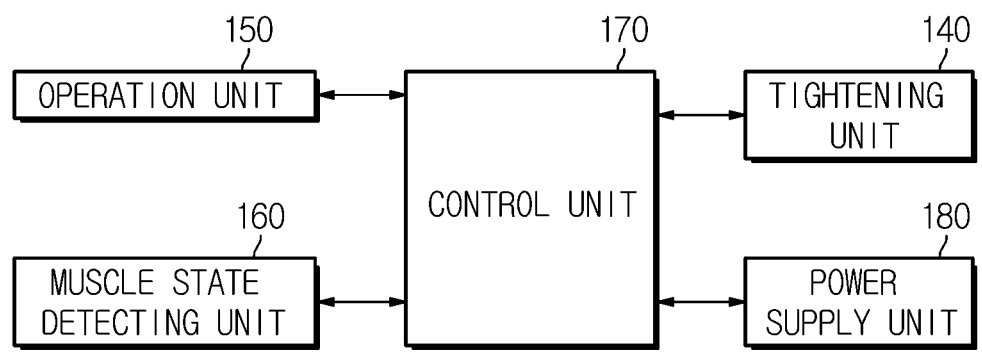
FIG. 4 is a block diagram illustrating a configuration of a muscular strength assisting apparatus according to some example embodiments.
Figure 5:
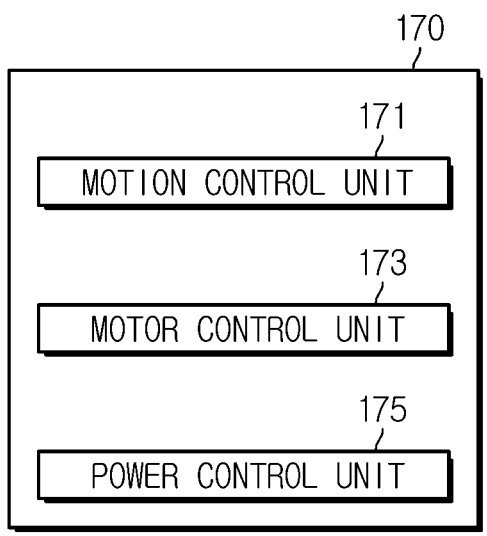
FIG. 5 is a block diagram illustrating a configuration of a control unit.
Figure 6:
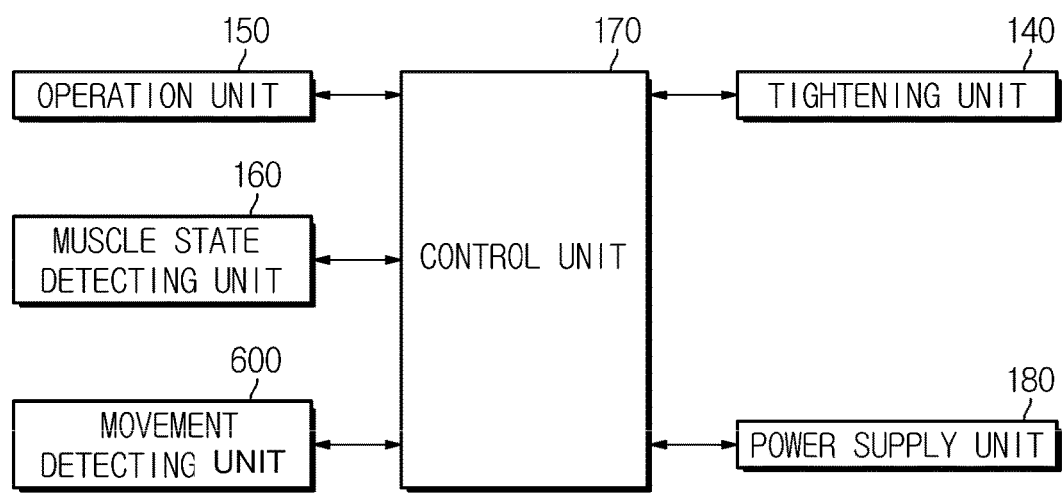
FIG. 6 is a block diagram illustrating a configuration of a muscular strength assisting apparatus according to some example embodiments.
Figure 7:
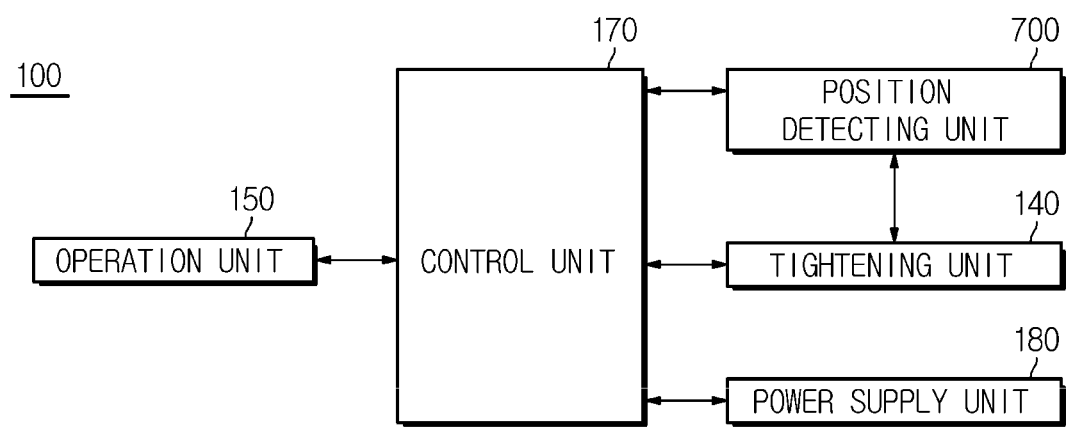
FIG. 7 is a block diagram illustrating a configuration of a muscular strength assisting apparatus according to some example embodiments.

FIG. 4 is a block diagram illustrating a configuration of a muscular strength assisting apparatus according to some example embodiments, FIG. 5 is a block diagram illustrating a configuration of a control unit, FIG. 6 is a block diagram illustrating a configuration of a muscular strength assisting apparatus according to some example embodiments, and FIG. 7 is a block diagram illustrating a configuration of a muscular strength assisting apparatus according to some example embodiments. The same components illustrated in FIGS. 4, 6, and 7 will be designated by the same reference numerals.

First of all, a configuration of a muscular strength assisting apparatus according to some example embodiments will be described with reference to FIG. 4.

Referring to FIG. 4, a muscular strength assisting apparatus 100 according to some example embodiments may include an operation unit 150, a muscle state detecting unit 160, a control unit 170, a tightening unit 140, and a power supply unit 180.

The operation unit 150 is configured to receive a command from a user and also to display an operating state of the muscular strength assisting apparatus 100 or an operated state thereof by the user so as to allow the user to check it, and may include a display 151 and a plurality of inputs 153, as illustrated in FIG. 3.

In some example embodiments, the display 151, which is configured to display an operated state of the inputs 153 by the user or the operating state of the muscular strength assisting apparatus 100, may include a liquid crystal display (LCD), a light emitting diode (LED), an organic light emitting diode (OLED), a plasma display panel (PDP), or a combination thereof, but is not particularly limited thereto.

Meanwhile, the display 151 according to some example embodiments may have a touchscreen structure which may receive the command from the user, but is not particularly limited thereto.

The inputs 153 serve to receive commands from the user, and may be provided in the form of buttons or the like, but are not particularly limited thereto. Also, FIG. 3 illustrates that three inputs 153 are provided, but this is just an example embodiment, and the number of inputs 153 is not particularly limited.

The three inputs 153 may include a power on/off button 153a, a setting button 153b, and a mode selecting button 153c. In some example embodiments, the power on/off button 153a is an input for supplying or cutting off power to the muscular strength assisting apparatus 100, and the setting button 153b is an input for tightening the wearing unit 120 of the muscular strength assisting apparatus 100 and, thus, fastening the muscular strength assisting apparatus 100 to a corresponding part of a user's body.

Also, the mode selecting button 153c is an input for selecting an operation mode of the muscular strength assisting apparatus 100. The operation mode of the muscular strength assisting apparatus 100 may include a stop mode, a position control mode, and a torque control mode, but is not particularly limited thereto.

Among them, the stop mode may be interpreted as a mode controlling the tightening unit 140 of the muscular strength assisting apparatus 100 not to be driven under any circumstances. For example, even though a muscle of the part of the user's body on which the muscular strength assisting apparatus 100 is located is contracted, the wearing unit 120 is maintained in an initial state and is not adapted to tighten the corresponding part of the user's body. It may be understood that the initial state of the wearing unit 120 is a tightening state at the time when the muscular strength assisting apparatus 100, which is installed at a part of a user's body, is fastened to the corresponding part of the user's body.

Therefore, when the stop mode is selected, the wearing unit 120 is maintained in the initial tightening state and thus tightened no further, even though the user applies a strain to the muscle of the part of the user's body on which the muscular strength assisting apparatus 100 is installed.

Also, the position control mode may be interpreted as a mode controlling the tightening unit 140 of the muscular strength assisting apparatus 100 to be maintained in an initial position. In order to perform the position control mode, a position detecting unit 700 detecting a position of the tightening unit 140 may be provided as illustrated in FIG. 7.

More specifically, in the position control mode, a current position of the tightening unit 140 is detected, a difference value between the detected current position and the initial position is calculated, and then the tightening unit 140 is controlled to compensate the calculated difference value (e.g., return to the initial position). It may be understood that the initial position of the tightening unit 140 is a position detected when the muscular strength assisting apparatus 100, which is installed at a part of a user's body, is fastened to the corresponding part of the user's body.

Further, the torque control mode may be interpreted as a mode determining whether muscular contraction occurs at the part of the user's body on which the muscular strength assisting apparatus 100 is located and then controlling an output torque of the tightening unit 140 so that the wearing unit 120 tightens the muscle of the corresponding part of the user's body when the muscular contraction occurs. In order to perform the torque control mode, a muscle state detecting unit 160 detecting a muscle activation state for determining whether the muscular contraction occurs may be provided as illustrated in FIG. 4.

In some example embodiments, the muscle state detecting unit 160 may be a myoelectric sensor, a force sensor, a torque-measuring device, or the like, but is not particularly limited thereto.

The myoelectric sensor is a sensor disposed at a part of a user's body, such as human arms and legs, and detecting an electromyographic signal changed according to a degree of the muscular contraction and, thus, measuring the muscle activation state. In some example embodiments, the electromyographic signal is an electric signal generated along a muscular fiber from a surface of the muscle according to a movement of the user's body. Since the electromyographic signal may be relatively easily detected compared to other bio-signals, such as an electroencephalogram (EEG) signal and an electrooculogram (EOG) signal, it is widely used in human-computer interface (HCI) technology.

As illustrated in FIG. 1, the myoelectric sensor may be disposed at an inner surface of the wearing unit 120 (e.g., a surface in contact with the user's body), and the number of myoelectric sensors is not particularly limited.

As described above, the muscle activation state of the part of the user's body, on which the muscular strength assisting apparatus 100 is located, may be detected by the myoelectric sensor provided at the inner surface of the wearing unit 120. For example, it is possible to detect the muscle activation state when the user applies a strain to the muscle of the part of the user's own body on which the muscular strength assisting apparatus 100 is installed. The detected muscle activation state is regarded as a current muscle activation state.

As described above, the detected current muscle activation state is provided to a control unit 170 to be described later. The control unit 170 may calculate the difference value between the current muscle activation state received from the myoelectric sensor and the initial muscle activation state, and then may provide a driving signal for outputting a torque proportional to the calculated difference value to the tightening unit 140. In some example embodiments, it may be understood that the 'initial muscle activation state' is a muscle activation state detected when the muscular strength assisting apparatus 100 is installed at a part of a user's body and then fastened to the corresponding part of the user's body (e.g., when the user does not apply a strain to the corresponding part of the user's own body).

The force sensor serves to detect a state that muscular fibers of the muscle to which the user's strain is applied are expanded (e.g., the muscle activation state). The force sensor may be also provided at an inner surface of the wearing unit 120, and the number of force sensors is not particularly limited.

As described above, the muscle activation state of the part of the user's body, on which the muscular strength assisting apparatus 100 is located, may be detected by the force sensor provided at the inner surface of the wearing unit 120. For example, if the user applies a strain to the muscle of the part of the user's own body on which the muscular strength assisting apparatus 100 is located, a volume of the muscle to which the user's strain is applied may be increased and, thus, a pressure may be applied to the force sensor due to the muscle having the increased volume. The force sensor converts the applied pressure into an electric signal and then outputs the electric signal to the control unit 170. The electric signal output from the force sensor to the control unit 170 may be a signal indicating the current muscle activation state. The electric signal indicating the current muscle activation state is regarded as a first electric signal.

The control unit 170 may calculate a difference value between the first electric signal received from the force sensor and a second electric signal indicating the initial muscle activation state, and then may provide a driving signal for outputting a force proportional to the calculated difference value to the tightening unit 140. In some example embodiments, it may be understood that the 'initial muscle activation state' is a muscle activation state detected when the muscular strength assisting apparatus 100 is installed at a part of a user's body and then fastened to the corresponding part of the user's body (e.g., when the user does not apply a strain to the corresponding part of the user's own body).

The torque-measuring device serves to measure an output torque of a motor when the motor is used for the tightening unit 140. That is, the torque-measuring device measures a change in the output torque of the tightening unit 140 and, thus, detects the muscle activation state.

For example, if the user applies a strain to the muscle of the part of the user's own body on which the muscular strength assisting apparatus 100 is located, a volume of the muscle to which the user's strain is applied is increased, and a pressure applied to the wearing unit 120 tightening the corresponding muscle is increased. If the pressure applied to the wearing unit 120 is increased, external force applied to the tightening unit 140 pulling the wearing unit 120 is increased. As the external force applied to the tightening unit 140 is increased, the torque output from the tightening unit 140 is changed, and the change in the output torque is measured using the torque-measuring device. Thus, it is possible to detect the muscle activation state.

The torque-measuring device may provide the measured output torque to the control unit 170. The output torque output from the torque-measuring device to the control unit 170 may be a signal indicating the current muscle activation state. The output torque indicating the current muscle activation state is regarded as a first output torque.

The control unit 170 may calculate a difference value between the first output torque received from the torque-measuring device and a second output torque indicating the initial muscle activation state and then may provide a driving signal for outputting a torque proportional to the calculated difference value to the tightening unit 140. In some example embodiments, it may be understood that the 'initial muscle activation state' is a muscle activation state detected when the muscular strength assisting apparatus 100 is installed at a part of a user's body and then fastened to the corresponding part of the user's body (e.g., when the user does not apply a strain to the corresponding part of the user's own body).

The tightening unit 140 serves to pull the wearing unit 120 in one direction or both directions and, thus, tighten the muscle of the part of the user's body on which the muscular strength assisting apparatus 100 is located. In some example embodiments, as illustrated in FIGS. 1 and 2, the tightening unit 140 may be provided at the other side of the body unit 110 so that the other end of the wearing unit 120 is connected with the body unit 110 and also pulled toward the body unit 110.

In some example embodiments, the motor may be used for the tightening unit 140, but is not particularly limited thereto. Further, in some example embodiments, the tightening unit 140 may further include a cylinder (not shown) which is provided to enclose the motor. Therefore, when the motor is driven, the other end of the wearing unit 120 is wound on an external surface of the cylinder, and the wearing unit 120 is pulled toward the body unit 110 and, thus, the muscle of the part of the user's body on which the wearing unit 120 is located is tightened.

The power supply unit 180 serves to supply power to the muscular strength assisting apparatus 100. In some example embodiments, the power supply unit 180 may be a battery, but is not particularly limited thereto. Since the muscular strength assisting apparatus 100 according to some example embodiments does not provide great strength, unlike the conventional wearing-type muscular strength assisting apparatus, the power supply unit 180 may have a low capacity and, thus, is light. Also, since the muscular strength assisting apparatus 100 according to some example embodiments does not provide great strength, it is possible to increase a use time of the power supply unit 180 due to a low power consumption of the muscular strength assisting apparatus 100.

The control unit 170 may control whole operations of the muscular strength assisting apparatus 100.

Specifically, as illustrated in FIG. 5, the control unit 170 may include a motion control unit 171, a motor control unit 173, and a power control unit 175, but is not particularly limited thereto.

The motion control unit 171 serves to generate a control signal which drives the tightening unit 140 so as to output a force corresponding to the muscle activation state detected through the command input from the user or the muscle state detecting unit 160. The control signal generated through the motion control unit 171 may be provided to the motor control unit 173.

The motor control unit 173 serves to substantially control driving of the motor according to the control signal received from the motion control unit 171. Specifically, the motor control unit 173 may convert the control signal received from the motion control unit 171 into a driving signal (e.g., an electric signal for driving the motor), may apply the converted electric signal to the motor, and thus may control the driving of the motor.

The power control unit 175 serves to apply power from the power supply unit 180 to each unit (e.g., the operation unit 150, the muscle state detecting unit 160, the control unit 170, and the tightening unit 140), and also to charge the power supply unit 180 from an external power source. Since the configuration of applying the power to the each unit and charging the power supply unit 180 from the external power source are already well known, description thereof will be omitted.

FIG. 6 is a block diagram illustrating a configuration of a muscular strength assisting apparatus according to some example embodiments. Some example embodiments further include a unit detecting whether the user is moving in the muscular strength assisting apparatus according to some example embodiments. Description of the parts corresponding to those in the muscular strength assisting apparatus according to some example embodiments discussed in this document will be omitted.

Referring to FIG. 6, the muscular strength assisting apparatus 100 according to some example embodiments may further include a movement detecting unit 600 which detects whether the user is moving, compared with the muscular strength assisting apparatus according to some other example embodiments.

In some example embodiments, the movement detecting unit 600 may be a motion sensor, but is not particularly limited thereto. In some example embodiments, the motion sensor may include an acceleration sensor, a gyro sensor, a terrestrial magnetism sensor, and so on, but is not particularly limited thereto.

That is, in the muscular strength assisting apparatus 100 according to some example embodiments, when it is detected that the user is moving, the tightening unit 140 is controlled not to be driven, even though a change in the muscle state of the user is detected.

This is to prevent that the wearing unit 120 tightens the user's muscle while the user is moving and, thus, the user is hindered in movements.

Figure 8:
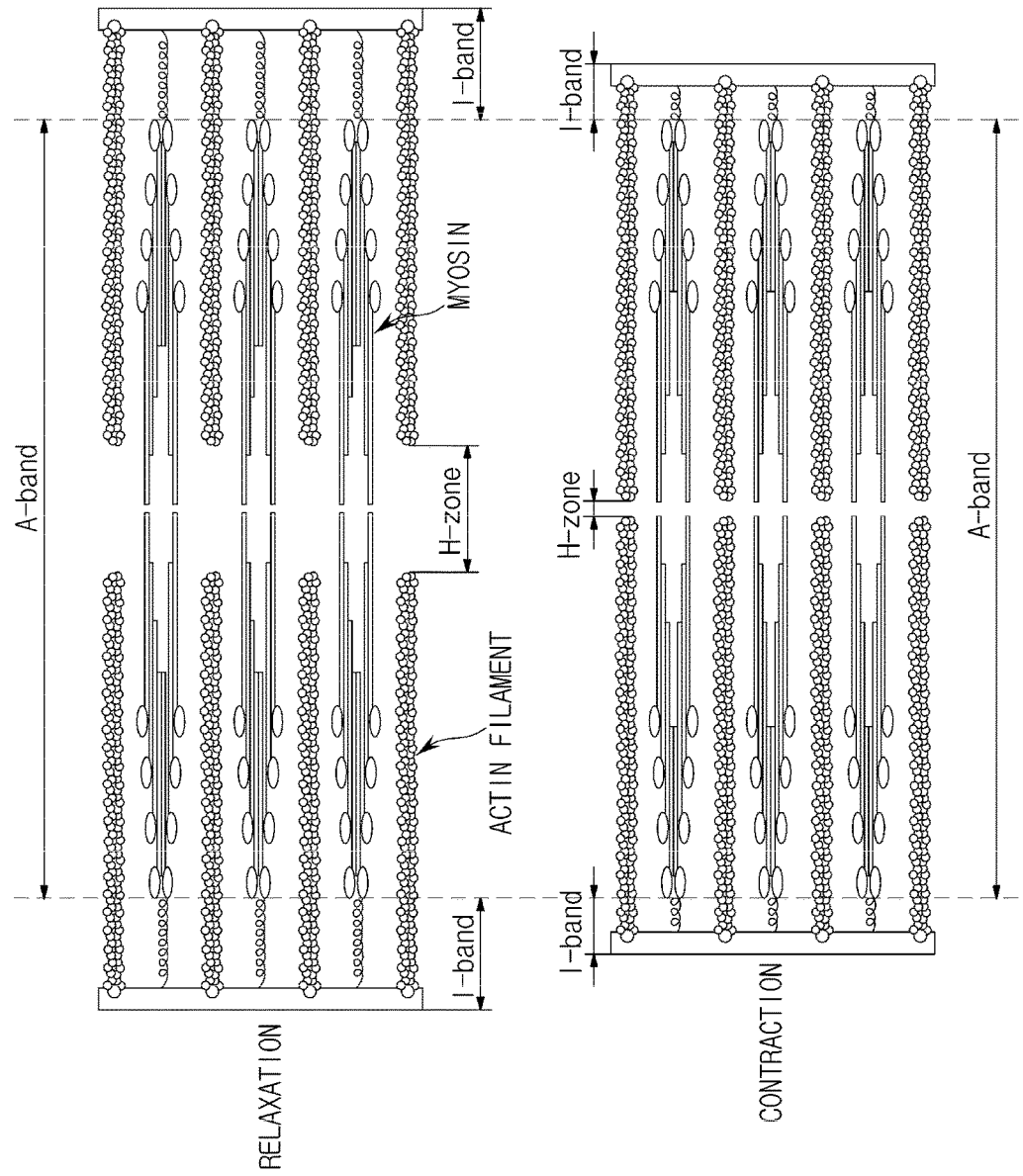
FIG. 8 is a conceptual diagram illustrating a principle of muscular contraction.

Generally, when a strain is applied to the muscle, the muscle is contracted. The muscular contraction may be caused by movement of filaments in a muscular fiber. Specifically, as illustrated in FIG. 8, the muscular contraction may be caused by cross-linkage between a thick filament, such as myosin protein conjugates, and a thin filament composed of actin proteins. The myosin or actin filament itself is not contracted, but the muscular contraction is caused by sliding between the actin filament and myosin molecules.

That is, referring to FIG. 8, the myosin is not changed, but the actin is moved, whereby the muscular contraction occurs. An A-band having the same length as the myosin is constant, and an I-band is changed according to contraction and relaxation of the muscle. Further, a length of an H-zone in the A-band is also changed according to the contraction and relaxation of the muscle. As described above, a change in a length of the muscle may be caused by the sliding between the two filaments (e.g., the myosin and the actin), instead of collision therebetween.

In some example embodiments, the A-band may be interpreted as a portion that the myosin filament and the actin filament are overlapped with each other, the I-band may be interpreted as a portion that only the actin filament exists, and the H-zone may be interpreted as a portion that only the myosin exists at a center of the A-band.

Meanwhile, it is well known that, if the muscular contraction is continuously maintained, the muscle gets gradually tired, and muscular contraction ability is reduced. As described above, if the muscular contraction ability is reduced, it is difficult to maintain the muscular contraction state.

Therefore, in order to continuously maintain the muscular contraction state, the muscular strength assisting apparatus 100 according to some example embodiments tightens the muscle and thus restrains movements of the actin filament and the myosin. That is, in a state in which the muscle is contracted, the contracted muscle is tightened by the wearing unit 120, and thus the movements of the actin filament and the myosin are restrained, whereby the user may maintain effortlessly the muscular contraction state.

Therefore, as fatigue of the contracted muscle is reduced, muscular endurance is increased, and thus the user may maintain a certain posture for a long time. Further, since the contracted muscle is tightened, it is possible to prevent a possibility that the muscle is damaged when the muscle is contracted. Furthermore, since a fixed point is additionally provided at a tightened part of the user's body, it is possible to reduce muscle activity.

Meanwhile, a lower limb muscle of a user who is walking may be repeatedly contracted and relaxed. However, in some example embodiments, the muscle is tightened using the wearing unit 120 in order to restrain the movements of the actin filament and the myosin, as described above and, thus, it is possible to assist the muscular strength which maintains the contracted state of the muscle.

That is, when it is necessary to continuously maintain the muscular contraction state, the muscular strength assisting apparatus 100 according to some example embodiments may more efficiently assist the muscular strength. However, if the muscular strength assisting apparatus 100 according to some example embodiments is applied to the user who is walking and, thus, whose muscle is repeatedly contracted and relaxed, the muscle is tightened even at a moment that it is necessary to relax the muscle, and the movements of the actin filament and the myosin are restrained. Thus, the user may be hindered in walking.

Therefore, the muscular strength assisting apparatus 100 according to some example embodiments may more effectively assist the muscular strength when the user takes a posture in which the user applies a strain to a corresponding muscle, but does not move. For example, the user takes and maintains one tense posture (e.g., a posture of bending and keeping the user's legs) in which the user applies to the corresponding muscle.

To this end, in some example embodiments, a speed of the movement of the user may be measured using the movement detecting unit 600, and the measured speed may be provided to the control unit 170. The control unit 170 may compare the speed of the movement of the user received from the movement detecting unit 600 with a desired threshold value (that may or may not be preset), and may decide that the user is moving, if the measured speed of the movement of the user is greater than or equal to the desired threshold value (that may or may not be preset) and, thus, may control the tightening unit 140 not to be driven.

Meanwhile, if the measured speed of the movement of the user is less than the desired threshold value (that may or may not be preset), the control unit 170 may decide that the user is not moving, and may control the tightening unit 140 according to a selected mode.

As described above, the mode selected by the user may include the stop mode, the position control mode, the torque control mode, and so on. In the stop mode, the tightening unit 140 may be controlled not to be driven, even when the muscular contraction occurs, and in the position control mode and the torque control mode, the muscle activation state may be detected, and the tightening unit 140 may be controlled to output a corresponding force according to the detected muscle activation state.

In other words, the muscular strength assisting apparatus 100 according to some example embodiments may decide whether the user is moving, and may control so that the user's muscle is not tightened, if the user is moving, and may control so that the user's muscle is not tightened or tightened with a tightening force corresponding to the user's muscle activation state, if the user is not moving.

FIG. 7 is a block diagram illustrating a configuration of a muscular strength assisting apparatus according to some example embodiments. Some example embodiments do not separately include the muscle state detecting unit detecting the change in the user's muscle state, unlike in the muscular strength assisting apparatus according to some example embodiments. Description of the parts corresponding to those in the muscular strength assisting apparatus according to some other example embodiments discussed in this document will be omitted.

Referring to FIG. 7, when compared to the muscular strength assisting apparatus according to some example embodiments, the muscular strength assisting apparatus 100 according to some example embodiments may include a position detecting unit 700 disposed at the tightening unit 140 and detecting position information of the tightening unit 140, instead of the muscle state detecting unit 160 detecting the change in the user's muscle state. That is, in some example embodiments, it is determined whether the muscular contraction occurs at the part of the user' body on which the wearing unit 120 is located using a change in the position of the tightening unit 140.

In some example embodiments, the position detecting unit 700 may be an encoder or a potentiometer, but is not particularly limited thereto.

For example, in a state in which the wearing unit 120 is fastened to a part of a user's body with a desired tightening force (that may or may not be predetermined), if the user applies a strain to the corresponding part of the user's own body, a volume of the muscle is increased and, thus, a pressure applied to the wearing unit 120 which tightens the muscle with the desired tightening force (that may or may not be predetermined) is also increased. Then, an external force applied to the tightening unit 140 pulling the wearing unit 120 is increased and, thus, the position of the tightening unit 140 is changed.

The position detecting unit 700 detects the changing position information, and then provides it to the control unit 170. The position information of the tightening unit 140 provided to the control unit 170 may be regarded as a current position. The control unit 170 which receives the current position of the tightening unit 140 from the position detecting unit 700, calculates a difference between an initial position of the tightening unit 140 and the current position, and controls the tightening unit 140 to compensate the calculated difference and return to the initial position.

In some example embodiments, the initial position of the tightening unit 140 may be regarded as a position when the muscular strength assisting apparatus 100 is installed at a part of a user's body and then fastened by a desired tightening force (that may or may not be predetermined).

As described above, if the tightening unit 140 is controlled to be always maintained at the initial position, a shape of the wearing unit 120 is constantly maintained so as to tighten the corresponding part of the user's body, even when the muscular contraction occurs.

Meanwhile, FIG. 5 illustrates a state of including only the position detecting unit 700 detecting the position information of the tightening unit 140, but example embodiments are not particularly limited thereto, and may further include the muscle state detecting unit 160 detecting the muscle activation state and the movement detecting unit 600 detecting the movement of the user.

Until now, the configurations of the muscular strength assisting apparatus 100 according to some example embodiments have been described. Hereinafter, controlling methods of the muscular strength assisting apparatus 100 according to some example embodiments will be described.

Figure 9:
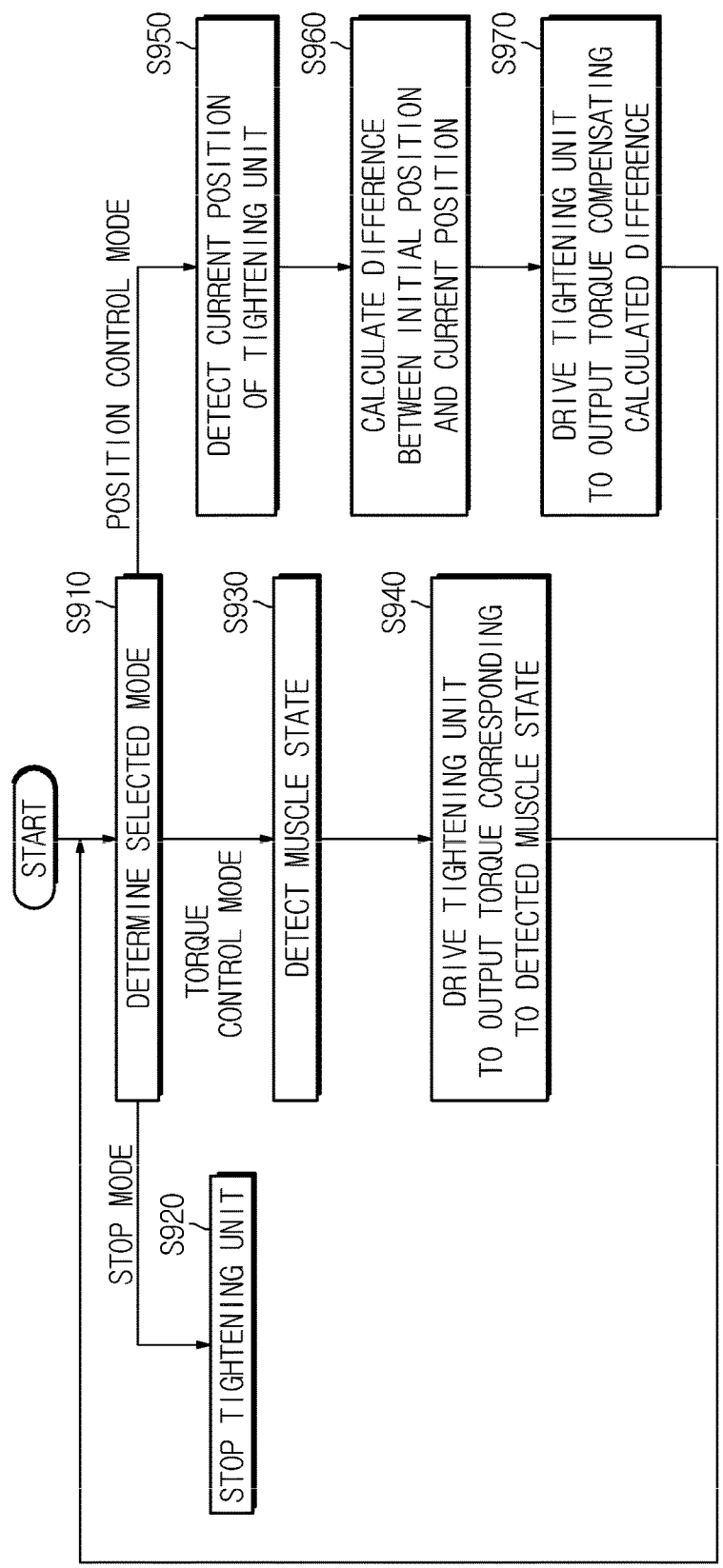
FIG. 9 is a flowchart illustrating a controlling method of the muscular strength assisting apparatus according to some example embodiments.

FIG. 9 is a flowchart illustrating a controlling method of the muscular strength assisting apparatus according to some example embodiments.

Referring to FIG. 9, the controlling method of the muscular strength assisting apparatus according to some example embodiments are as follows.

First of all, it is determined what mode is selected by a user (S910).

In some example embodiments, the "mode" may be interpreted as an operation mode of the muscular strength assisting apparatus 100, and may include a stop mode, a position control mode, and a torque control mode, but is not particularly limited thereto.

The stop mode may be interpreted as a mode controlling the tightening unit 140 of the muscular strength assisting apparatus 100 not to be driven, the position control mode may be interpreted as a mode controlling the tightening unit 140 to be maintained at the initial position, and the torque control mode may be interpreted as a mode controlling the output torque of the tightening unit 140 to output a corresponding torque according to the muscle activation state of the part of the user's body on which the muscular strength assisting apparatus 100 is located.

Meanwhile, even though not illustrated in FIG. 9, before performing the operation S910, the controlling method may further include an operation of fastening the muscular strength assisting apparatus 100 to the corresponding part of the user's body by the user and selecting the operation mode.

For example, the muscular strength assisting apparatus 100 is installed on a part of a user's body, for example, which needs assistance of the muscular strength, and power is supplied to the muscular strength assisting apparatus 100 using the power on/off button 153*a* of the operation unit 150, and then the tightening unit 140 is driven using the setting button 153*b* so that the wearing unit 120 tightens the corresponding part of the user's body. Thus, the muscular strength assisting apparatus 100 may be fastened to the corresponding part of the user's body. After fastening of the muscular strength assisting apparatus 100, the tightening unit 140 may be in a stopped state. Then, the user may set a desired assisting manner for the muscular strength using the mode selecting button 153*c*.

As a result of the determination, if the selected mode by the user is the 'stop mode', the tightening unit 140 is maintained in the stopped state (S920). In the stopped state, even though a certain change occurs at the muscle of the part of the user's body on which the muscular strength assisting apparatus 100 is located (e.g., the muscular contraction occurs), the wearing unit 120 is maintain in the initial state and, thus, does not tighten the corresponding part of the user's body any more. It may be understood that the initial state of the wearing unit 120 is a tightening state when the muscular strength assisting apparatus 100, which is installed on the part of the user's body, is tightened with a desired tightening force (that may or may not be predetermined), as described above.

Meanwhile, as a result of the determination, if the selected mode by the user is the 'torque control mode', as illustrated in FIG. 9, the change in the muscle state (e.g., the muscle activation state of the part of the user's body), on which the muscular strength assisting apparatus 100 is located, is detected (S930), and then the tightening unit 140 is driven to output a corresponding torque according to the detected muscle activation state (S940). That is, the output torque of the tightening unit 140 is controlled so that the wearing unit 120 tightens the muscle of the corresponding part of the user's body according to the muscle activation state of the part of the user's body, on which the muscular strength assisting apparatus 100 is located.

In some example embodiments, the operation S930 of detecting the muscle activation state of the part of the user's body, on which the muscular strength assisting apparatus 100 is located, may be performed through various manners.

In a first manner, a myoelectric sensor is provided at an inner surface of the wearing unit 120 and measures an electromyographic signal generated from the muscle of the corresponding part of the user's body. The myoelectric sensor is a sensor attached to each part of the user's body, such as arms and legs, and detecting the electromyographic signal differently generated according to a degree of the muscular contraction and, thus, measuring the muscle activation state. In some example embodiments, the electromyographic signal is an electric signal generated along a muscular fiber from the surface of the muscle according to the movement of the user's body. That is, the occurrence of the muscular contraction at the corresponding part of the user's body may be detected by using the myoelectric sensor.

In a second manner, a force sensor provided at the inner surface of the wearing unit 120 is used. That is, if a volume of the muscle of the part of the user's body, on which the muscular strength assisting apparatus 100 is located, is increased by the movement of the user, a pressure is applied to the wearing unit 120 by the muscle having the increased volume and, thus, applied to the force sensor. The force sensor converts the applied pressure into an electric signal and then outputs the converted electric signal to the control unit 170. That is, the increase in the volume of the muscle due to the occurrence of the muscular contraction at the corresponding part of the user's body may be detected by using the force sensor.

In a third manner, a change in the torque output from the tightening unit 140 is measured by using a torque-measuring device. That is, the change in the output torque of the tightening unit 140 is measured and, thus, the muscle activation state is detected. For example, if the volume of the muscle of the part of the user's body, on which the muscular strength assisting apparatus 100 is located, is increased by the movement of the user, the pressure applied to the wearing unit 120 tightening the corresponding part of the user's body is also increased and, thus, an external force applied to the tightening unit 140 pulling the wearing unit 120 is increased. As the external force applied to the tightening unit 140 is increased, the torque output from the tightening unit 140 is changed, and the change in the output torque is measured by using the torque-measuring device. Thus, the occurrence of the muscle contraction at the corresponding part of the user's body may be detected.

Further, the operation S940 of driving the tightening unit 140 so as to output the corresponding torque according to the detected muscle activation state may be performed through a manner corresponding to each detecting manner of the muscle activation state.

For example, when the electromyographic signal is detected using the myoelectric sensor, the myoelectric sensor may detect the electromyographic signal at the part of the user's body, on which the muscular strength assisting apparatus 100 is located, and then may provide the detected electromyographic signal to the control unit 170.

The control unit 170 may calculate a difference value between the electromyographic signal received from the myoelectric sensor and an initial electromyographic signal, and then may provide a driving signal, which outputs a torque proportional to the calculated difference value to the tightening unit 140. In some example embodiments, it may be understood that the 'initial electromyographic signal' is an electromyographic signal detected when the muscular strength assisting apparatus 100 is fastened to the corresponding part of the user's body (e.g., before the user applies a strain to the muscle).

Further, when the change in the muscle state is detected using the force sensor, the force sensor may detect force information applied by expansion of the muscle of the part of the user's body, on which the muscular strength assisting apparatus 100 is located, and then may provide the detected force information to the control unit 170.

The control unit 170 may calculate a difference value between the force information received from the force sensor and initial force information, and then may provide a driving signal, which outputs a torque proportional to the calculated difference value to the tightening unit 140. In some example embodiments, it may be understood that the 'initial force information' is force information detected when the muscular strength assisting apparatus 100 is fastened to the corresponding part of the user's body (e.g., force information corresponding to force applied to the force sensor before the user applies a strain to the muscle).

Further, when the change in the muscle state is detected using the torque-measuring device, the torque-measuring device may measure the output torque of the tightening unit 140, which is changed by the external force applied to the tightening unit 140 according to the increase in the volume of the muscle of the part of the user's body, on which the muscular strength assisting apparatus 100 is located, and then may provide the measured output torque to the control unit 170.

The control unit 170 may calculate a difference value between the output torque received from the torque-measuring device and an initial output torque, and then may provide a driving signal, which outputs a torque proportional to the calculated difference value to the tightening unit 140. In some example embodiments, it may be understood that the 'initial output torque' is an output torque detected when the muscular strength assisting apparatus 100 is fastened to the corresponding part of the user's body (e.g., an output torque of the tightening unit 140 detected before the user applies a strain to the muscle).

Meanwhile, as a result of the determination, if the selected mode by the user is the position control mode, as illustrated in FIG. 9, a current position of the tightening unit 140 is detected (S950), a difference value between the detected current position and an initial position is calculated (S960), and then the tightening unit 140 is driven to output a torque compensating the calculated difference value (S970). That is, the tightening unit 140 is controlled to return to the initial position. It may be understood that the initial position of the tightening unit 140 is a position of the tightening unit 140 which is detected using the position detecting unit 700, when the muscular strength assisting apparatus 100 is fastened to the corresponding part of the user's body.

In some example embodiments, the operation S950 of detecting the current position of the tightening unit 140 may be performed using the position detecting unit 700 provided at the tightening unit 140. The position detecting unit 700 may be an encoder or a potentiometer, but is not particularly limited thereto.

The method of FIG. 9 may be used in more general purpose systems and/or for methods of controlling such systems. For example, the method may be used in various automated systems and/or for controlling such systems so as to allow safe startup, operation, and/or shutdown of the systems.

FIG. 10 is a flowchart illustrating a controlling method of the muscular strength assisting apparatus according to some example embodiments. Some example embodiments may further include an operation of determining whether the user is moving in the controlling method of the muscular strength assisting apparatus according to some other example embodiments. In some example embodiments, description of the operations corresponding to those in the controlling method according to some other example embodiments discussed in this document will be omitted.

Referring to FIG. 10, the controlling method of the muscular strength assisting apparatus according to some example embodiments is as follows.

First of all, it is determined whether a user is moving (S1010). In some example embodiments, it may be understood that the 'moving' may be interpreted as 'walking', but example embodiments are not particularly limited thereto.

In some example embodiments, an operation of determining whether the user is moving may be performed using the movement detecting unit 600 illustrated in FIG. 6. The movement detecting unit 600 may be a motion sensor, but is not particularly limited thereto. In some example embodiments, the motion sensor may include an acceleration sensor, a gyro sensor, a terrestrial magnetism sensor, and so on, but is not particularly limited thereto.

That is, in some example embodiments, when it is determined that the user is moving, the tightening unit 140 is controlled not to be driven, even though a change in the muscle state of the user is detected. This is to prevent that the wearing unit 120 tightens the user's muscle, while the user is moving and, thus, the user is hindered in movements. Since this was already described above, description thereof will be omitted.

As a result of the determination, if it is determined that the user is moving, the driving of the tightening unit 140 is stopped (S1020), and if it is determined that the user is not moving, it is determined what mode is selected by the user (S1030).

As a result of the determination, if the selected mode by the user is the 'stop mode', the tightening unit 140 is maintained in the stopped state (S1020). That is, in a state in which the user is not moving, the wearing unit 120 does not tighten the corresponding part of the user's body any more, even though the muscle state of the user is changed.

Further, as a result of the determination, if the selected mode by the user is the 'torque control mode', the muscle activation state of the part of the user's body on which the muscular strength assisting apparatus 100 is located is detected (S1040), and then the tightening unit 140 is driven to output a corresponding torque according to the detected muscle activation state (S1050). That is, the output torque of the tightening unit 140 is controlled so that the wearing unit 120 tightens the muscle of the corresponding part of the user's body according to a degree of the muscular contraction of the part of the user's body on which the muscular strength assisting apparatus 100 is located.

The operation S1040 of detecting the muscle activation state of the part of the user's body, on which the muscular strength assisting apparatus 100 is located, may be performed through various manners, as follows.

In a first manner, the myoelectric sensor is provided at the inner surface of the wearing unit 120, and measures an electromyographic signal generated from the muscle. In a second manner, the force sensor is provided at the inner surface of the wearing unit 120, and measures a force applied according to the increase in the volume of the muscle. In a third manner, the change in the torque output from the tightening unit 140 is measured using the torque-measuring device. Each manner was already described above and, thus, description thereof will be omitted.

Further, the operation S1050 of driving the tightening unit 140 so as to output a corresponding torque according to the detected muscle activation state may be performed through a manner corresponding to each detecting manner of the muscle activation state.

For example, when the electromyographic signal is measured using the myoelectric sensor, the myoelectric sensor may measure the electromyographic signal at the part of the user's body, on which the muscular strength assisting apparatus 100 is located, and then may provide the measured electromyographic signal to the control unit 170. The control unit 170 may calculates a difference value between the electromyographic signal received from the myoelectric sensor and an initial electromyographic signal, and then may provide a driving signal, which outputs a torque proportional to the calculated difference value to the tightening unit 140.

Further, when the force according to the increase in the volume of the muscle is measured using the force sensor, the force sensor may detect a force applied by expansion of the muscle of the part of the user's body, on which the muscular strength assisting apparatus 100 is located, and then may provide the detected force to the control unit 170. The control unit 170 may calculate a difference value between the force received from the force sensor and an initial force, and then may provide a driving signal, which outputs a torque proportional to the calculated difference value to the tightening unit 140.

Further, when the muscle activation state is detected using the torque-measuring device, the torque-measuring device may measure the output torque of the tightening unit 140, which is changed by the external force applied to the tightening unit 140 due to the pressure applied to the wearing unit 120 according to the increase in the volume of the muscle of the part of the user's body on which the muscular strength assisting apparatus 100 is located, and then may provide the measured output torque to the control unit 170. The control unit 170 may calculate a difference value between the output torque received from the torque-measuring device and an initial output torque, and then may provide a driving signal, which outputs a torque proportional to the calculated difference value to the tightening unit 140.

Meanwhile, as a result of the determination, if the selected mode by the user is the position control mode, as illustrated in FIG. 10, a current position of the tightening unit 140 is detected (S1060), a difference value between the detected current position and an initial position is calculated (S1070), and then the tightening unit 140 is driven to output a torque compensating the calculated difference value (S1080). That is, the tightening unit 140 is controlled to return to the initial position.

The operation S1060 of detecting the current position of the tightening unit 140 may be performed using the position detecting unit 700 provided at the tightening unit 140. The position detecting unit 700 may be an encoder or a potentiometer, but is not particularly limited thereto.

The method of FIG. 10 may be used in more general purpose systems and/or for methods of controlling such systems. For example, the method may be used in autonomous devices and/or for controlling such devices so as to allow safe deployment, operation, and/or retrieval of the devices.

The algorithms discussed in this application (e.g., required to control the muscular strength assisting apparatuses) may be used in more general purpose apparatuses and/or methods of controlling apparatuses. For example, the algorithms may be used in apparatuses for handling hazardous materials and/or for controlling such apparatuses so as to allow safe movement, packaging, and/or shipment of hazardous materials.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to muscular strength assisting apparatuses, those skilled in the art will appreciate that some example embodiments may be applied to other types of systems, such as systems not used in the medical field (e.g., aerospace teleoperation systems, apparatuses for handling hazardous materials, patrol apparatuses, military apparatuses), humanoid apparatuses, or more general purpose control systems. Those skilled in the art will appreciate that the muscular strength assisting apparatuses described in this application have a myriad of practical uses.

Although some example embodiments have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A muscular strength assisting apparatus, comprising:
    a wearing unit configured to enclose a part of a user's body;
    a tightening unit configured to pull the wearing unit in at least one direction;
    a muscle state detector configured to detect a muscular contraction occurring at the part of the user's body that is enclosed by the wearing unit;
    a position detector configured to detect position information of the tightening unit;
    a memory storing a program; and
    a processor configured to execute the program to,
        drive the tightening unit to tighten the part of the user's body that is enclosed by the wearing unit, based on a determination that the muscular contraction occurs at the part of the user's body that is enclosed by the wearing unit, the driving including,
        detecting a current muscle activation state associated with the part of the user's body that is enclosed by the wearing unit, based on the muscle state detector and a current position of the tightening unit using the position detector,
        calculating a difference between the detected current muscle activation state and an initial muscle activation state and a difference between the detected current position of the tightening unit and an initial position of the tightening unit, and
        driving the tightening unit to output a force or torque proportional to the calculated difference between the detected current muscle activation state and the initial muscle activation state and to output a force or torque proportional to the calculated difference between the detected current position of the tightening unit and the initial position of the tightening unit and compensating the calculated difference between the detected current position of the tightening unit and the initial position of the tightening unit.

2. The apparatus according to claim 1, further comprising:
    a movement detector configured to detect whether the user is moving.

3. The apparatus according to claim 2, the processor configured to execute the program to,
    detect a moving speed of the user using the movement detector,
    based on determining whether the user is moving based on the detected moving speed, perform one of,
        stop the tightening unit based on a determination that the user is moving, and
        drive the tightening unit based on a determination that the user is not moving.

4. The apparatus according to claim 1, wherein the tightening unit includes a motor.

5. The apparatus according to claim 1, further comprising:
    an operation unit having a plurality of inputs configured to receive commands from the user.

6. The apparatus according to claim 5, wherein the operation unit further includes a display configured to display an operating state of the muscular strength assisting apparatus and an operated state of the inputs by the user.

7. A method of controlling a muscular strength assisting apparatus, comprising:
    determining whether muscular contraction occurs at a part of a user's body that is enclosed by a wearing unit based on detecting a muscle activation state associated with the part of the user's body that is enclosed by the wearing unit; and
    driving a tightening unit pulling the wearing unit in one direction or both directions to tighten the part of the user's body that is enclosed by the wearing unit based on a determination that the muscular contraction occurs at the part of the user's body that is enclosed by the wearing unit, the driving including,
        calculating a difference value between the detected muscle activation state and an initial muscle activation state; and a difference value between a detected position of the tightening unit and an initial position of the tightening unit, and
        driving the tightening unit to output a force or torque proportional to the calculated difference value between the detected muscle activation state and the initial muscle activation state and to output a force or torque proportional to the calculated difference value between the detected position of the tightening unit and the initial position of the tightening unit and compensating the calculated difference value between the detected position of the tightening unit and the initial position of the tightening unit.

8. The method according to claim 7, further comprising:
    determining a mode set by the user before the determining of whether the muscular contraction occurs.

9. The method according to claim 8, wherein the mode set by the user comprises a stop mode, a torque control mode, or a position control mode.

10. The method according to claim 9, wherein after the determining of the mode set by the user, if the mode set by the user is the stop mode, the tightening unit is in a stopped state, even though the muscular contraction occurs at the part of the user's body that is enclosed by the wearing unit.

11. The method according to claim 9, further comprising:
    performing the determining of whether the muscular contraction occurs subsequently to performing the determining of the mode set by the user, based on a determination that the mode set by the user is the torque control mode.

12. The method according to claim 9, wherein after the determining of the mode set by the user, if the mode set by the user is the position control mode, the determining of whether the muscular contraction occurs is performed by detecting a position of the tightening unit.

13. The method according to claim 7, further comprising:
   determining whether the user is moving, before the determining of whether the muscular contraction occurs.

14. The method according to claim 13, wherein after the determining of whether the user is moving, if the user is moving, the tightening unit is in a stopped state, even though the muscular contraction occurs at the part of the user's body that is enclosed by the wearing unit and if the user is not moving, the tightening unit is driven so that the wearing unit tightens the part of the user's body that is enclosed by the wearing unit, when the muscular contraction occurs at the part of the user's body that is enclosed by the wearing unit.

* * * * *